United States Patent
Young et al.

(10) Patent No.: US 7,252,821 B2
(45) Date of Patent: Aug. 7, 2007

(54) CANCEROUS DISEASE MODIFYING ANTIBODIES

(75) Inventors: David S. F. Young, Toronto (CA); Helen P. Findlay, Toronto (CA); Susan E. Hahn, Toronto (CA); Miyoko Takahashi, North York (CA)

(73) Assignee: Arius Research Inc., Ontario (CA)

( * ) Notice: Subject to any disclaimer, the term of this patent is extended or adjusted under 35 U.S.C. 154(b) by 531 days.

(21) Appl. No.: 10/603,000

(22) Filed: Jun. 23, 2003

(65) Prior Publication Data

US 2004/0105815 A1 Jun. 3, 2004

Related U.S. Application Data

(63) Continuation-in-part of application No. 09/727,361, filed on Nov. 29, 2000, now Pat. No. 6,657,048, which is a continuation-in-part of application No. 09/415,278, filed on Oct. 8, 1999, now Pat. No. 6,180,357.

(51) Int. Cl.
*A61K 39/395* (2006.01)
*G01N 33/574* (2006.01)
*C12P 21/08* (2006.01)
*C07K 16/00* (2006.01)
*C12P 21/04* (2006.01)

(52) U.S. Cl. .............. 424/141.1; 424/133.1; 424/143.1; 424/155.1; 424/181.1; 435/7.23; 435/69.6; 435/70.21; 530/387.3; 530/388.1; 530/388.22; 530/388.8; 530/391.7

(58) Field of Classification Search ............. 530/387.1, 530/387.3, 388.1, 388.22, 388.8, 391.7; 424/130.1, 424/133.1, 141.1, 143.1, 155.1, 181.1; 435/69.6, 435/70.21, 7.23
See application file for complete search history.

(56) References Cited

U.S. PATENT DOCUMENTS

| | | | |
|---|---|---|---|
| 4,172,124 A | 10/1979 | Koprowski et al. |
| 4,861,581 A | 8/1989 | Epstein et al. |
| 5,171,665 A | 12/1992 | Hellstrom et al. |
| 5,484,596 A | 1/1996 | Hanna, Jr. et al. |
| 5,530,101 A | * | 6/1996 | Queen et al. |
| 5,693,763 A | 12/1997 | Codington et al. |
| 5,750,102 A | 5/1998 | Eisenbach et al. |
| 5,780,033 A | 7/1998 | Torchilin et al. |
| 5,783,186 A | 7/1998 | Arakawa et al. |
| 5,849,876 A | 12/1998 | Linsley et al. |
| 5,869,045 A | 2/1999 | Hellstrom et al. |
| 5,869,268 A | 2/1999 | Kudo et al. |
| 6,180,357 B1 | 1/2001 | Young et al. |
| 6,657,048 B2 | 12/2003 | Young et al. |
| 2002/0041877 A1 | 4/2002 | Young et al. |
| 2004/0001789 A1 | 1/2004 | Young et al. |

FOREIGN PATENT DOCUMENTS

| | | |
|---|---|---|
| WO | WO95/20401 | 8/1995 |
| WO | WO02/082076 | 10/2002 |
| WO | WO03/055515 | 7/2003 |

OTHER PUBLICATIONS

Campbell et al. Biology, 5th ed. p. 856, 1999.*
Co et al. Nature, 351(6):501-502, Jun. 6, 1991.*
D. Harris et al, "Serotherapy of cancer", Seminars in Oncology, 16(3):180-198 (Jun. 1989).
H. Dvorak et al, "Structure of solid tumors and their vasculature: implications for therapy with monoclonal antibodies", Cancer Cells, 3(3):77-85 (Mar. 1991).
S. Engelholm et al, "Disaggregation of human solid tumours by combined mechanical and enzymatic methods", Br. J. Cancer, 51:93-98 (1985).
A. Costa et al, "Implications of disaggregation procedures on biological representation of human solid tumours", Cell Tisue Kinet., 20:171-180 (1987).
S. Dairkee et al, "Partial enzymatic degradation of stroma allows enrichment and expansion of primary breast tumor cells", Cancer Research, 57:1590-1596 (Apr. 1997).
B. Franzen et al, "Nonenzymatic extraction of cells from clinical tumor material for analysis of gene expression by two-dimensional polyacrylamide gel electrophoresis", Electrophoresis, 14:1045-1053 (1993).
E. Holz et al, "Antibody-based immunotherapeutic strategies in colorectal cancer", Recent Results in Cancer Research, 142:381-400 (1996).
R. Dillman, "Antibodies as cytotoxic therapy", J. Clin. Oncol., 12(7):1497-1515 (Jul. 1994).
R. Dillman, "Monoclonal antibodies for treating cancer", Annals of Internal Medicine, 111:592-603 (1989).
M. Disis et al, "HER-2/neu protein: a target for antigen-specific immunotherapy of human cancer", Advances in Cancer Research, 71:343-371 (1997).
A. Begg et al, "Rapid fluorescence-based assay for radiosensitivity and chemosensitivity testing in mammalian cells in vitro", Cancer Research, 49:565-569 (Feb. 1989).
J. Cruse et al, Illustrated Dictionary of Immunology, CRC Press, p. 280 (1995).

(Continued)

*Primary Examiner*—Sheela J. Huff
*Assistant Examiner*—David J. Blanchard
(74) *Attorney, Agent, or Firm*—McHale & Slavin, P.A.

(57) ABSTRACT

The present invention relates to a method for producing patient cancerous disease modifying antibodies using a novel paradigm of screening. By segregating the anti-cancer antibodies using cancer cell cytotoxicity as an end point, the process makes possible the production of anti-cancer antibodies for therapeutic and diagnostic purposes. The antibodies can be used in aid of staging and diagnosis of a cancer, and can be used to treat primary tumors and tumor metastases. The anti-cancer antibodies can be conjugated to toxins, enzymes, radioactive compounds, and hematogenous cells.

13 Claims, 13 Drawing Sheets
(6 of 13 Drawing Sheet(s) Filed in Color)

OTHER PUBLICATIONS

A. Knuth et al, "ADCC reactivity of human melanoma cels with mouse monoclonal antibodies", Proc. Am. Assoc. Cancer Res., 25:1005 (Mar. 1984) Abstract only.

J. Horoszewicz et al, "Monoclonal antibodies to a new antigenic marker in epithelial prostatic cells and serum of prostatic cancer patients", Anticancer Research, 7:927-936 (1987).

D. Herlyn et al, "Monoclonal anticolon carcinoma antibodies in complement-dependent cytotoxicity", Int. J. Cancer, 27:769-774 (1981).

V. Kravtsov et al, "Automated monitoring of apoptosis in suspension cell cultures", Laboratory Investigation, 74(2):557-570 (1996).

L. Hartwell et al, "Integrating genetic approaches into the discovery of anticancer drugs", Science, 278:1064-1068 (Nov. 1997).

B. Curti, "Physical barriers to drug delivery in tumors", Critical Reviews in Oncology/Hematology, 14:29-39 (1993).

R. Jain, "Barriers to drug delivery in solid tumors", Scientific American, 271(1):58-65 (Jul. 1994).

T. Gura, "Systems for identifying new drugs are often faulty", Science, 278:1041-1042 (Nov. 1997).

G. Dermer, "Another anniversary for the war on cancer", Bio/Technology, 12:320 (Mar. 1994).

R. Freshney, "Culture of animal cells", a Manual of Basic Technique, Alan R. Liss, Inc., New York, p. 3 (1983).

T. Hsu, "Karyology of cells in culture—a preparation and analysis of karotypes and idiograms", in Tissue Culture Methods and Applications, eds. Kruse and Patterson, Academic Press, New York, pp. 764-767 (1973).

M. Embleton, "Monoclonal antibodies to osteogenic sarcoma antigens", Immunol. Ser., 23:181-207 (1984).

H. Drexler, "Recent results on the biology of Hodgkin and Reed-Stemberg cells", Leukemia and Lymphoma, 9:1-25 (1993).

C. Badger et al, "Prospects for monoclonal antibody therapy of leukemia and lymphoma", Cancer, 58:584-589 (1986).

E. Boven et al, "Monoclonal antibodies in cancer treatment: where do we stand after 10 years?", Radiotherapy and Oncology, 5:109-117 (1986).

A. Epstein et al, "Two new monoclonal antibodies, Lym-1 and Lym-2, reactive with human B-lymphocytes and derived tumors, with immunodiagnostic and immunotherapeutic potential", Cancer Research, 47:830-840 (1987).

K. Foon, "Biological therapy of cancer", Breast Cancer Research & Treatment, 7:5-14 (1986).

* cited by examiner

A.

B.

C.

A.

B.

C.

A.

B.

C.

A.

B.

C.

CANCEROUS DISEASE MODIFYING ANTIBODIES

REFERENCE TO RELATED APPLICATIONS

This application is a continuation-in-part of application Ser. No. 09/727,361, filed Nov. 29, 2000, now U.S. Pat. No. 6,657,048 B2, issued Dec. 2, 2003, which is a continuation-in-part of application Ser. No. 09/415,278, filed Oct. 8, 1999, now U.S. Pat. No. 6,180,357 B1, issued Jan. 30, 2001, the contents of each of which are herein incorporated by reference.

FIELD OF THE INVENTION

This invention relates to the isolation and production of cancerous disease modifying antibodies (CDMAB) and to the use of these CDMAB in therapeutic and diagnostic processes, optionally in combination with one or more chemotherapeutic agents. The invention further relates to binding assays which utilize the CDMAB of the instant invention.

BACKGROUND OF THE INVENTION

Each individual who presents with cancer is unique and has a cancer that is as different from other cancers as that person's identity. Despite this, current therapy treats all patients with the same type of cancer, at the same stage, in the same way. At least 30 percent of these patients will fail the first line therapy, thus leading to further rounds of treatment and the increased probability of treatment failure, metastases, and ultimately, death. A superior approach to treatment would be the customization of therapy for the particular individual. The only current therapy that lends itself to customization is surgery. Chemotherapy and radiation treatment cannot be tailored to the patient, and surgery by itself, in most cases is inadequate for producing cures.

With the advent of monoclonal antibodies, the possibility of developing methods for customized therapy became more realistic since each antibody can be directed to a single epitope. Furthermore, it is possible to produce a combination of antibodies that are directed to the constellation of epitopes that uniquely define a particular individual's tumor.

Having recognized that a significant difference between cancerous and normal cells is that cancerous cells contain antigens that are specific to transformed cells, the scientific community has long held that monoclonal antibodies can be designed to specifically target transformed cells by binding specifically to these cancer antigens; thus giving rise to the belief that monoclonal antibodies can serve as "Magic Bullets" to eliminate cancer cells.

Monoclonal antibodies isolated in accordance with the teachings of the instantly disclosed invention have been shown to modify the cancerous disease process in a manner which is beneficial to the patient, for example by reducing the tumor burden, and will variously be referred to herein as cancerous disease modifying antibodies (CDMAB) or "anti-cancer" antibodies.

At the present time, the cancer patient usually has few options of treatment. The regimented approach to cancer therapy has produced improvements in global survival and morbidity rates. However, to the particular individual, these improved statistics do not necessarily correlate with an improvement in their personal situation.

Thus, if a methodology was put forth which enabled the practitioner to treat each tumor independently of other patients in the same cohort, this would permit the unique approach of tailoring therapy to just that one person. Such a course of therapy would, ideally, increase the rate of cures, and produce better outcomes, thereby satisfying a long-felt need.

Historically, the use of polyclonal antibodies has been used with limited success in the treatment of human cancers. Lymphomas and leukemias have been treated with human plasma, but there were few prolonged remission or responses. Furthermore, there was a lack of reproducibility and no additional benefit compared to chemotherapy. Solid tumors such as breast cancers, melanomas and renal cell carcinomas have also been treated with human blood, chimpanzee serum, human plasma and horse serum with correspondingly unpredictable and ineffective results.

There have been many clinical trials of monoclonal antibodies for solid tumors. In the 1980s there were at least 4 clinical trials for human breast cancer which produced only 1 responder from at least 47 patients using antibodies against specific antigens or based on tissue selectivity. It was not until 1998 that there was a successful clinical trial using a humanized anti-her 2 antibody in combination with cis-platin. In this trial 37 patients were accessed for responses of which about a quarter had a partial response rate and another half had minor or stable disease progression.

The clinical trials investigating colorectal cancer involve antibodies against both glycoprotein and glycolipid targets. Antibodies such as 17-1A, which has some specificity for adenocarcinomas, had undergone Phase 2 clinical trials in over 60 patients with only 1 patient having a partial response. In other trials, use of 17-1A produced only 1 complete response and 2 minor responses among 52 patients in protocols using additional cyclophosphamide. Other trials involving 17-1A yielded results that were similar. The use of a humanized murine monoclonal antibody initially approved for imaging also did not produce tumor regression. To date there has not been an antibody that has been effective for colorectal cancer. Likewise there have been equally poor results for lung, brain, ovarian, pancreatic, prostate, and stomach cancers. There has been some limited success in the use of anti-GD3 monoclonal antibody for melanoma. Thus, it can be seen that despite successful small animal studies that are a prerequisite for human clinical trials, the antibodies that have been tested thus far, have been for the most part, ineffective.

PRIOR PATIENTS

U.S. Pat. No. 5,750,102 discloses a process wherein cells from a patient's tumor are transfected with MHC genes which maybe cloned from cells or tissue from the patient. These transfected cells are then used to vaccinate the patient.

U.S. Pat. No. 4,861,581 discloses a process comprising the steps of obtaining monoclonal antibodies that are specific to an internal cellular component of neoplastic and normal cells of the mammal but not to external components, labeling the monoclonal antibody, contacting the labeled antibody with tissue of a mammal that has received therapy to kill neoplastic cells, and determining the effectiveness of therapy by measuring the binding of the labeled antibody to the internal cellular component of the degenerating neoplastic cells. In preparing antibodies directed to human intracellular antigens, the patentee recognizes that malignant cells represent a convenient source of such antigens.

U.S. Pat. No. 5,171,665 provides a novel antibody and method for its production. Specifically, the patent teaches formation of a monoclonal antibody which has the property of binding strongly to a protein antigen associated with human tumors, e.g. those of the colon and lung, while binding to normal cells to a much lesser degree.

U.S. Pat. No. 5,484,596 provides a method of cancer therapy comprising surgically removing tumor tissue from a human cancer patient, treating the tumor tissue to obtain tumor cells, irradiating the tumor cells to be viable but non-tumorigenic, and using these cells to prepare a vaccine for the patient capable of inhibiting recurrence of the primary tumor while simultaneously inhibiting metastases. The patent teaches the development of monoclonal antibodies which are reactive with surface antigens of tumor cells. As set forth at col. 4, lines 45 et seq., the patentees utilize autochthonous tumor cells in the development of monoclonal antibodies expressing active specific immunotherapy in human neoplasia.

U.S. Pat. No. 5,693,763 teaches a glycoprotein antigen characteristic of human carcinomas is not dependent upon the epithelial tissue of origin.

U.S. Pat. No. 5,783,186 is drawn to anti-Her2 antibodies which induce apoptosis in Her2 expressing cells, hybridoma cell lines producing the antibodies, methods of treating cancer using the antibodies and pharmaceutical compositions including said antibodies.

U.S. Pat. No. 5,849,876 describes new hybridoma cell lines for the production of monoclonal antibodies to mucin antigens purified from tumor and non-tumor tissue sources.

U.S. Pat. No. 5,869,268 is drawn to a method for generating a human lymphocyte producing an antibody specific to a desired antigen, a method for producing a monoclonal antibody, as well as monoclonal antibodies produced by the method. The patent is particularly drawn to the production of an anti-HD human monoclonal antibody useful for the diagnosis and treatment of cancers.

U.S. Pat. No. 5,869,045 relates to antibodies, antibody fragments, antibody conjugates and single chain immunotoxins reactive with human carcinoma cells. The mechanism by which these antibodies function is two-fold, in that the molecules are reactive with cell membrane antigens present on the surface of human carcinomas, and further in that the antibodies have the ability to internalize within the carcinoma cells, subsequent to binding, making them especially useful for forming antibody-drug and antibody-toxin conjugates. In their unmodified form the antibodies also manifest cytotoxic properties at specific concentrations.

U.S. Pat. No. 5,780,033 discloses the use of autoantibodies for tumor therapy and prophylaxis. However, this antibody is an anti-nuclear autoantibody from an aged mammal. In this case, the autoantibody is said to be one type of natural antibody found in the immune system. Because the autoantibody comes from "an aged mammal", there is no requirement that the autoantibody actually comes from the patient being treated. In addition the patent discloses natural and monoclonal anti-nuclear autoantibody from an aged mammal, and a hybridoma cell line producing a monoclonal anti-nuclear autoantibody.

BRIEF SUMMARY OF THE INVENTION

The instant inventors have previously been awarded U.S. Pat. No. 6,180,357, entitled "Individualized Patient Specific Anti-Cancer Antibodies" directed to a process for selecting individually customized anti-cancer antibodies which are useful in treating a cancerous disease. For the purpose of this document, the terms "antibody" and "monoclonal antibody" (mAb) may be used interchangeably and refer to intact immunoglobulins produced by hybridomas, immunoconjugates and, as appropriate, immunoglobulin fragments and recombinant proteins derived from immunoglobulins, such as chimeric and humanized immunoglobulins, F(ab') and F(ab')$_2$ fragments, single-chain antibodies, recombinant immunoglobulin variable regions (Fv)s etc. Furthermore, it is within the purview of this invention to conjugate standard chemotherapeutic modalities, e.g. radionuclides, with the CDMAB of the instant invention, thereby focusing the use of said chemotherapeutics. The CDMAB can also be conjugated to toxins, cytotoxic moieties or enzymes e.g. biotin conjugated enzymes.

This application utilizes the method for producing patient specific anti-cancer antibodies as taught in the '357 patent for isolating hybridoma cell lines which encode for cancerous disease modifying monoclonal antibodies. These antibodies can be made specifically for one tumor and thus make possible the customization of cancer therapy. Within the context of this application, anti-cancer antibodies having either cell-killing (cytotoxic) or cell-growth inhibiting (cytostatic) properties will hereafter be referred to as cytotoxic. These antibodies can be used in aid of staging and diagnosis of a cancer, and can be used to treat tumor metastases.

The prospect of individualized anti-cancer treatment will bring about a change in the way a patient is managed. A likely clinical scenario is that a tumor sample is obtained at the time of presentation, and banked. From this sample, the tumor can be typed from a panel of pre-existing cancerous disease modifying antibodies. The patient will be conventionally staged but the available antibodies can be of use in further staging the patient. The patient can be treated immediately with the existing antibodies and/or a panel of antibodies specific to the tumor can be produced either using the methods outlined herein or through the use of phage display libraries in conjunction with the screening methods herein disclosed. All the antibodies generated will be added to the library of anti-cancer antibodies since there is a possibility that other tumors can bear some of the same epitopes as the one that is being treated. The antibodies produced according to this method may be useful to treat cancerous disease in any number of patients who have cancers that bind to these antibodies.

Accordingly, it is an objective of the invention to utilize a method for producing cancerous disease modifying antibodies from cells derived from a particular individual which are cytotoxic with respect to cancer cells while simultaneously being relatively non-toxic to non-cancerous cells, in order to isolate hybridoma cell lines and the corresponding isolated monoclonal antibodies and antigen binding fragments thereof for which said hybridoma cell lines are encoded.

It is an additional objective of the invention to teach CDMAB and antigen binding fragments thereof.

It is a further objective of the instant invention to produce CDMAB whose cytotoxicity is mediated through ADCC.

It is yet an additional objective of the instant invention to produce CDMAB whose cytotoxicity is mediated through CDC.

It is still a further objective of the instant invention to produce CDMAB whose cytotoxicity is a function of their ability to catalyze hydrolysis of cellular chemical bonds.

A still further objective of the instant invention is to produce CDMAB which are useful for in a binding assay for diagnosis, prognosis, and monitoring of cancer.

Other objects and advantages of this invention will become apparent from the following description wherein are set forth, by way of illustration and example, certain embodiments of this invention.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
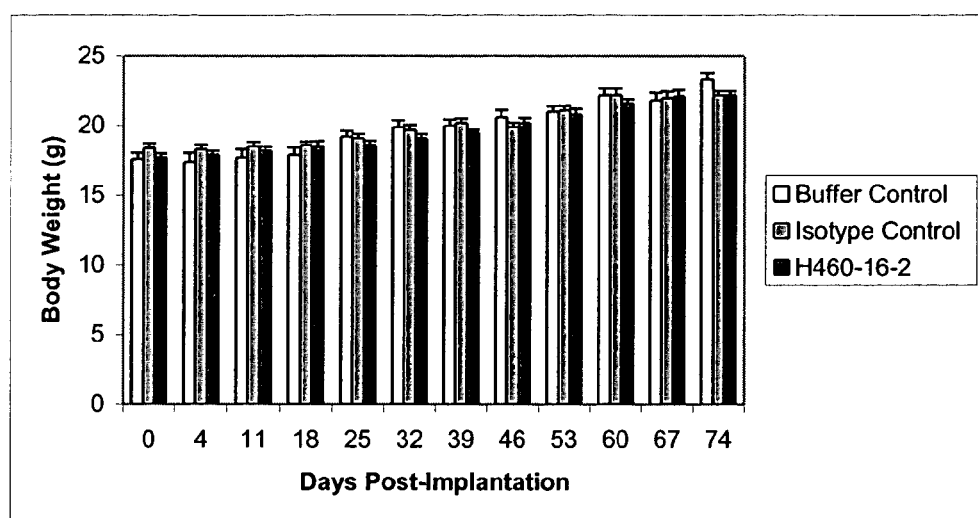
FIG. 1. Histogram showing mean body weight of the different treatment groups over the duration of the study. Data are presented as the mean+/−SEM for each group at each time point.

Using substantially the process of U.S. Pat. No. 6,180,357, the mouse monoclonal antibody H460-16-2 was obtained following immunization of mice with cells from a patient's lung tumor biopsy. The H460-16-2 antigen was expressed on the cell surface of a broad range of human cell lines from different tissue origins. The breast cancer cell line MDA-MB-231 (MB-231) was only 1 of 2 cancer cell lines tested that was susceptible to the cytotoxic effects of H460-16-2.

The result of H460-16-2 cytotoxicity against MB-231 cells in culture was further extended by its anti-tumor activity towards these cells when transplanted into mice. In an in vivo model of breast cancer, the human MB-231 cells were implanted underneath the skin at the scruff of the neck of immunodeficient mice, as they are incapable of rejecting the human tumor cells due to a lack of certain immune cells. Pre-clinical xenograft tumor models are considered valid predictors of therapeutic efficacy. Xenografts in mice grow as solid tumors developing stroma, central necrosis and neo-vasculature. The mammary tumor cell line MB-231 has been evaluated as an in vivo xenograft model in immuno-deficient mice. The good engrafiment or 'take-rate' of the MB-231 tumors and the sensitivity of the tumors to standard chemotherapeutic agents have characterized it as a suitable model. The parental cell line and variants of the cell line have been used in xenograft tumor models to evaluate a wide range of therapeutic agents.

In the preventative in vivo model of human breast cancer, H460-16-2 was given to mice one day prior to implantation of tumor cells followed by weekly injections for a period of 7 weeks. H460-16-2 treatment was significantly ($p<0.0001$) more effective in suppressing tumor growth during the treatment period than an isotype control antibody, which was identical to H460-16-2 in structure and size but incapable of binding MB-231 cells. At the end of the treatment phase, mice given H460-16-2 had tumors that grew to only 1.3 percent of the control group. During the post treatment follow-up period, the treatment effects of H460-16-2 were sustained and the mean tumor volume in the treated groups continued to be significantly smaller than controls until the end of the measurement phase. Using survival as a measure of antibody efficacy, it was estimated that the risk of dying in the H460-16-2 treatment group was about 71 percent of the antibody buffer control group ($p=0.028$) at 70 days post-treatment. These data demonstrated that H40-16-2 treatment conferred a survival benefit compared to the control-treated groups. H460-16-2 treatment appeared safe, as it did not induce any signs of toxicity, including reduced body weight and clinical distress. Thus, H460-16-2 treatment was efficacious as it both delayed tumor growth and enhanced survival compared to the control-treated groups in a well-established model of human breast cancer. These results were also reproducible as similar findings were observed in another study of this kind and suggest its relevance and benefit to treatment of people with cancer.

Besides the preventative in vivo tumor model of breast cancer, H460-16-2 demonstrated anti-tumor activity against MB-231 cells in an established in vivo tumor model. In this xenograft tumor model, MB-231 breast cancer cells were transplanted subcutaneously into immunodeficient mice such that the tumor reached a critical size before antibody treatment. Treatment with H460-16-2 was compared to the standard chemotherapeutic drug, cisplatin, and it was shown that the cisplatin and H460-16-2 treatment groups had significantly ($p<0.001$) smaller mean tumor volumes compared with groups treated with either antibody dilution buffer or the isotype control antibody. H460-16-2 treatment mediated tumor suppression that was approximately two-thirds that of cisplatin chemotherapy but without the significant weight loss ($p<0.003$) and clinical distress observed with cisplatin. The anti-tumor activity of H460-16-2 and its minimal toxicity make it an attractive anti-cancer therapeutic agent.

In the post-treatment period, H460-16-2 showed a significant survival benefit (p<0.02) as the risk of dying in the H460-16-2 group was about half of that in the isotype control antibody group at >70 days after treatment. The observed survival benefit continued on at 120 days post-treatment where 100 percent of the isotype control and cisplatin treated mice had died compared to 67 percent of the H460-16-2 treatment group. H460-16-2 maintained tumor suppression by delaying tumor growth by 26 percent compared to the isotype control antibody group. At 31 days post treatment, H460-16-2 limited tumor size by reducing tumor growth by 48 percent compared to the isotype control group, which is comparable to the 49 percent reduction observed at the end of the treatment. In the established tumor model of breast cancer, these results indicate the potential of H460-16-2 to maintain tumor suppression beyond the treatment phase and demonstrates the ability of the antibody to reduce the tumor burden and enhance survival in a mammal.

By immunohistochemistry (IHC) staining, sections of mouse tissues from multiple organs were stained with H460-16-2 to localize the H460-16-2 antigen within individual cell types of various tissues. Consistent with the tumor suppressive effects of H460-16-2 against MB-231 cells in vivo, the H460-16-2 antigen was strongly expressed on sections of tumor tissue harvested from untreated mice subcutaneously implanted with MB-231 cells. Expression of the H460-16-2 antigen in normal mouse tissues is required for supporting the mouse as an appropriate model of toxicity for H460-16-2. It was observed that the H460-16-2 antigen had a limited expression pattern in the mouse as it was only expressed in the kidney and ovary. In order to validate the mouse as a suitable model for toxicity, there needs to be similar antigen expression in normal human tissue.

For clinical trials and to validate an appropriate animal model for toxicity, the specificity of H460-16-2 towards normal human tissues was determined. By IHC staining with H460-16-2, the majority of the tissues failed to express the H460-16-2 antigen, including the vital organs, such as the liver, kidney, heart, and lung. H460-16-2 stained the skin, ureter, stomach and prostate, and strongly stained the salivary gland. Results from tissue staining indicated that H460-16-2 showed restricted binding to various cell types but had binding to infiltrating macrophages, lymphocytes, and fibroblasts. Therefore, the data indicate that the mouse is probably not the best model for toxicity since that although both the mouse and human show limited H460-16-2 tissue expression; the tissues positive for staining are not the same between the two species.

Localization of the H460-16-2 antigen and its prevalence within breast cancer patients is important in assessing the benefits of H460-16-2 immunotherapy to patients and designing effective clinical trials. To address H460-16-2 antigen expression in breast tumors from cancer patients, tumor tissue samples from 50 individual breast cancer patients were screened for expression of the H460-16-2 antigen. The results of the study showed that 64 percent of tissue samples stained positive for the H460-16-2 antigen. Expression of H460-16-2 within patient samples appeared specific for cancer cells as staining was restricted towards malignant cells. In contrast, H460-16-2 stained 2 of 9 samples of normal tissue from breast cancer patients. Breast tumor expression of the H460-16-2 antigen appeared to be mainly localized to the cell membrane of malignant cells, making it an attractive target for therapy. H460-16-2 expression was further evaluated based on breast tumor expression of the receptors for the hormones estrogen and progesterone, which play an important role in the development, treatment, and prognosis of breast tumors. No correlation was apparent between expression of the H460-16-2 antigen and expression of the receptors for either estrogen or progesterone. When tumors were analyzed based on their stage, or degree to which the cancer advanced, results suggested a trend towards greater positive expression with higher tumor stage, but the results were limited by the small sample size.

To further extend the potential therapeutic benefit of H460-16-2, the frequency and localization of the antigen within various human cancer tissues was determined. Several cancer types, besides breast, were positive for the H460-16-2 antigen. The positive human cancer types included skin (1/2), lung (4/4), liver (2/3), stomach (4/5) and kidney (3/3). Some cancers did not express the antigen; these included ovary (0/3), adrenal gland (0/2) and small intestine (0/1). As with human breast tumor tissue, localization occurred predominately on the membrane of tumor cells. So, in addition to the H460-16-2 antibody binding to cancer cell lines in vitro, there is evidence that the antigen is expressed in humans, and on multiple types of cancers. In toto, this data demonstrates that the H460-16-2 antigen is a cancer associated antigen and is expressed in humans, and is a pathologically relevant cancer target. Further, this data also demonstrates the binding of the H460-16-2 antibody to human cancer tissues, and can be used appropriately for assays that can be diagnostic, predictive of therapy, or prognostic. In addition, the cell membrane localization of this antigen is indicative of the cancer status of the cell due to the lack of expression of the antigen in most non-malignant cells, and this observation permits the use of this antigen, its gene or derivatives, its protein or its variants to be used for assays that can be diagnostic, predictive of therapy, or prognostic.

Preliminary data indicate that the antigen recognized by H460-16-2 could be a variant of the tumor rejection antigen known as the 96 kDa heat shock protein (gp96). This is supported by biochemical studies showing that monoclonal antibodies reactive against gp96 identify proteins that were bound to H460-16-2. By IHC analysis of mouse tissues using H460-16-2 and anti-gp96 antibodies, the gp96 antigen appeared to be more widely expressed than the H460-16-2 antigen. These results were similar to those for IHC staining of normal human tissues as the H460-16-2 antigen was expressed on a smaller subset of cells compared to the gp96 antigen. IHC analysis of human breast tumor tissues indicated that the gp96 antigen was more prevalent with approximately 84 percent of samples staining positive with the anti-gp96 antibody. The gp96 antigen was also expressed differently than H460-16-2 as it showed both high cytoplasmic and cell membrane localization. These results thus suggest that H460-16-2 may be a variant of gp96.

In all, this invention teaches the use of the H460-16-2 antigen as a target for a therapeutic agent, that when administered can reduce the tumor burden of a cancer expressing the antigen in a mammal, and can also lead to a prolonged survival of the treated mammal. This invention also teaches the use of a CDMAB (H460-16-2), and its derivatives, to target its antigen to reduce the tumor burden of a cancer expressing the antigen in a mammal, and to prolong the survival of a mammal bearing tumors that express this antigen. Furthermore, this invention also teaches the use of detecting the H460-16-2 antigen in cancerous cells that can be useful for the diagnosis, prediction of therapy, and prognosis of mammals bearing tumors that express this antigen.

If a patient is refractory to the initial course of therapy or metastases develop, the process of generating specific antibodies to the tumor can be repeated for re-treatment. Furthermore, the anti-cancer antibodies can be conjugated to red blood cells obtained from that patient and re-infused for treatment of metastases. There have been few effective treatments for metastatic cancer and metastases usually portend a poor outcome resulting in death. However, metastatic cancers are usually well vascularized and the delivery of anti-cancer antibodies by red blood cells can have the effect of concentrating the antibodies at the site of the tumor. Even prior to metastases, most cancer cells are dependent on the host's blood supply for their survival and anti-cancer antibody conjugated to red blood cells can be effective against in situ tumors as well. Alternatively, the antibodies may be conjugated to other hematogenous cells, e.g. lymphocytes, macrophages, monocytes, natural killer cells, etc.

There are five classes of antibodies and each is associated with a function that is conferred by its heavy chain. It is generally thought that cancer cell killing by naked antibodies are mediated either through antibody-dependent cell-mediated cytotoxicity (ADCC) or complement-dependent cytotoxicity (CDC). For example murine IgM and IgG2a antibodies can activate human complement by binding the C-1 component of the complement system thereby activating the classical pathway of complement activation which can lead to tumor lysis. For human antibodies, the most effective complement activating antibodies are generally IgM and IgG1. Murine antibodies of the IgG2a and IgG3 isotype are effective at recruiting cytotoxic cells that have Fc receptors which will lead to cell killing by monocytes, macrophages, granulocytes and certain lymphocytes. Human antibodies of both the IgG1 and IgG3 isotype mediate ADCC.

Another possible mechanism of antibody mediated cancer killing may be through the use of antibodies that function to catalyze the hydrolysis of various chemical bonds in the cell membrane and its associated glycoproteins or glycolipids, so-called catalytic antibodies.

There are two additional mechanisms of antibody mediated cancer cell killing which are more widely accepted. The first is the use of antibodies as a vaccine to induce the body to produce an immune response against the putative antigen that resides on the cancer cell. The second is the use of antibodies to target growth receptors and interfere with their function or to down regulate that receptor so that effectively its function is lost.

EXAMPLE 1

The hybridoma cell line H460-16-2 was deposited, in accordance with the Budapest Treaty, with the American Type Culture Collection, 10801 University Blvd., Manassas, Va. 20110-2209 on Sep. 4, 2002, under Accession Number PTA-462 1. In accordance with 37 CFR 1.808, the depositors assure that all restrictions imposed on the availability to the public of the deposited materials will be irrevocably removed upon the granting of a patent.

H460-16-2 monoclonal antibody was produced by culturing the hybridomas in CL-1000 flasks (BD Biosciences, Oakville, ON) with collections and reseeding occurring twice/week and was purified according to standard antibody purification procedures with Protein G Sepharose 4 Fast Flow (Amersham Biosciences, Baie d'Urfé, QC).

In Vivo Preventative Tumor Experiments

With reference to the data shown in FIGS. 1 and 2, 4 to 8 week old, female SCID mice were implanted with 5 million MB-231 human breast cancer cells in 100 microliters saline injected subcutaneously in the scruff of the neck. The mice were randomly divided into 3 treatment groups of 10. On the day prior to implantation 20 mg/kg of H460-16-2 test antibody, antibody buffer or isotype control antibody (known not to bind MB-231 cells) was administered intraperitoneally at a volume of 300 microliters after dilution from the stock concentration with a diluent that contained 2.7 mM KCl, 1 mM $KH_2PO_4$, 137 mM NaCl and 20 mM $Na_2HPO_4$. The antibodies were then administered once per week for a period of 7 weeks in the same fashion.

Tumor growth was measured roughly every 7th day with calipers for up to 10 weeks or until individual animals reached the Canadian Council for Animal Care (CCAC) end-points or day 120. Body weights of the animals were recorded for the duration of the study. At the end of the study all animals were euthanised according to CCAC guidelines.

The data presented in this study is a typical example of a longitudinal data set. Usually, in such data sets there are high correlations among time-points and higher correlations are observed between closer time-points. Because of this, repeated measures analysis of variance (Rep. ANOVA) was used to determine the differences among treatments and the method of analysis of covariance was used to determine the time-points when differences occurred. The latter is a suitable method when the differences among groups at each time-point may not be just due to groups but may be due to the previous time-points.

There were no clinical signs of toxicity throughout the study. Body weight measured at weekly intervals was a surrogate for well-being and failure to thrive. FIG. 1 represents the mean body weight of mice for the 3 groups over the study period. Body weights within each group increased over time. Rep. ANOVA indicated that there was no significant difference among groups and the mean profiles do not differ over time-points for the groups treated with isotype control, antibody buffer or H460-16-2.

Figure 2:
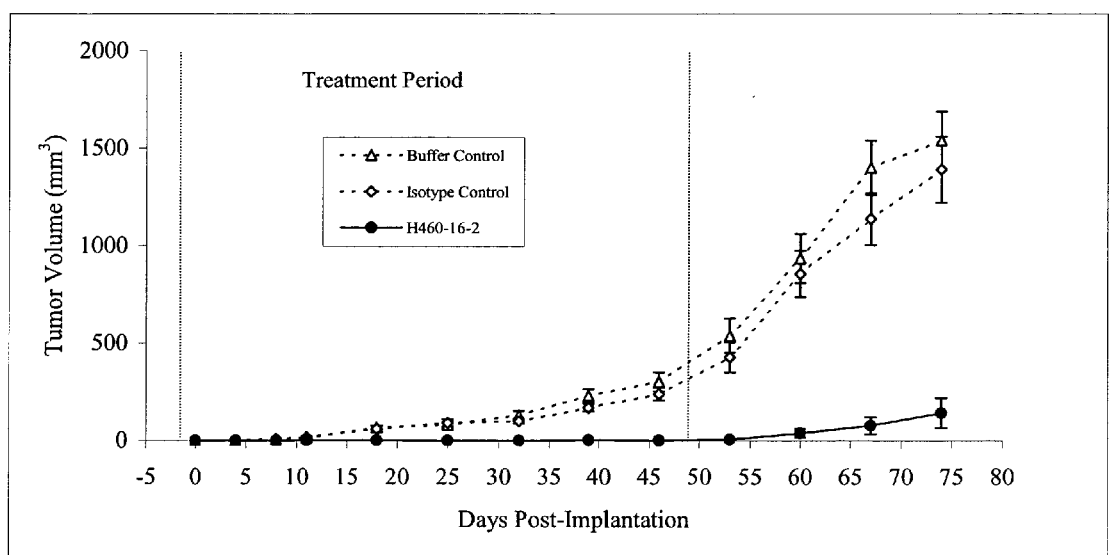
FIG. 2. Effect of H460-16-2 on tumor growth in a preventative MB-231 breast cancer model. The dashed line indicates the period during which the antibody was administered. Data points represent the mean+/−SEM.
Figure 3:
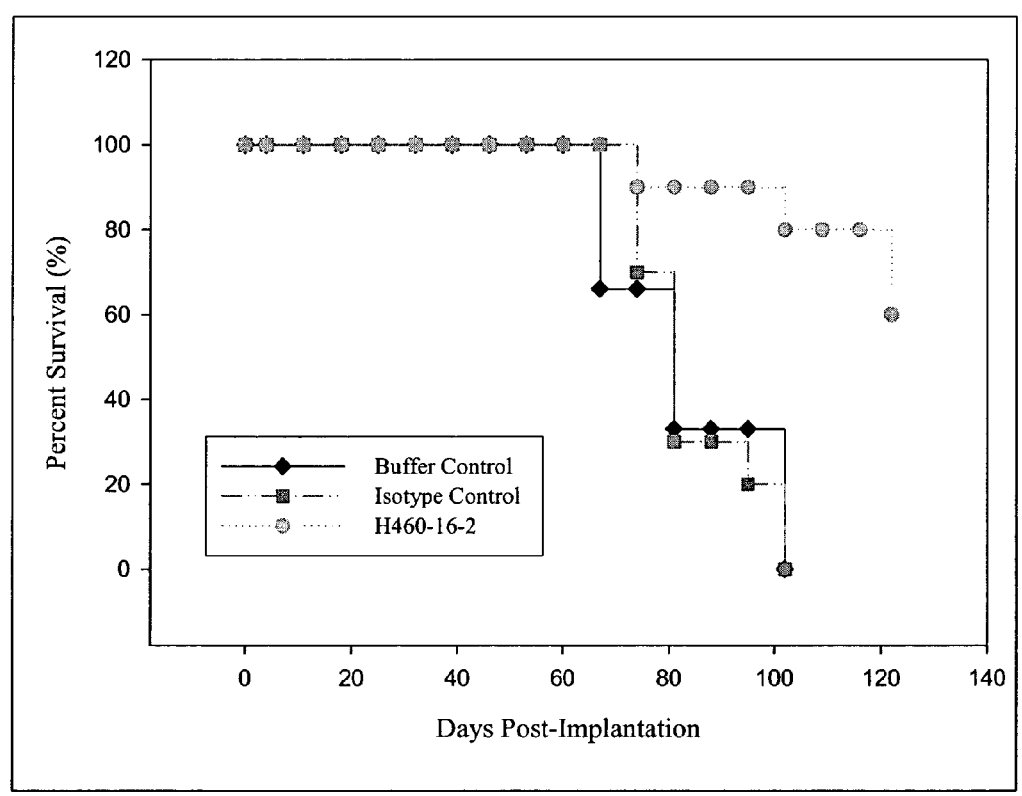
FIG. 3. Survival of tumor-bearing mice after treatment with H460-16-2, buffer and isotype control antibody. Mice were monitored for survival for over 70 days post-treatment.

Using Rep. ANOVA for the whole experiment, the following results were noticeable. The Rep. ANOVA method indicated that not only the means of the groups were different ($p<0.001$) but also the shapes of the mean profiles differed from each other. As can be seen in FIG. 2, treatment group H460-16-2 seemed to have a superior effect compared to the other groups. In addition, the difference between the isotype control treated group and the antibody buffer treated group was not statistically significant. From analysis of covariance, significant differences occurred for the first time at day 18, where isotype and buffer treatment groups differed from the H460-16-2 treatment group. At day 53, (the first tumor volume measurement after the cessation of treatment) tumor volume of the group treated with H460-16-2 was 1.3% of the antibody control treated group ($p<0.0001$) thereby demonstrating effectiveness at preventing tumor burden. There was also a corresponding survival benefit (FIG. 3) from treatment with H460-16-2. Enhanced survival is a valuable indicator of efficacy. All 3 groups were followed for over 70 days post-treatment. The Cox proportional hazard test estimates that the risk of dying in in ARH460-16-2 group was about 71% of the buffer control group ($p=0.028$). These data demonstrate that treatment with the test antibody confers a survival benefit compared to control-treated groups. Control groups reached 50% mortality between day 74–81 post-implantation. In contrast, treated groups had not reached 50% mortality at the time of termination of the study (day 120 post-implantation). The isotype control group treatment group reached 100% mortality by day 74 post-implantation. In contrast, H460-16-2 treated animals displayed 60% survival at the end of the study.

In summary, H460-16-2 antibody treatment prevented tumor burden and increased survival in comparison to a control antibody in a well-recognized model of human cancer disease. These results suggest a potential pharmacologic and pharmaceutical benefit of this antibody (H460-16-2) as a therapy in other mammals, including man.

EXAMPLE 2

In Vivo Established Tumor Experiments

Female SCID mice, 5 to 6 weeks old, were implanted with 5 million MB-231 breast cancer cells in 100 microliters saline injected subcutaneously in the scruff of the neck. Tumor growth was measured with calipers every week. When the majority of the cohort reached a tumor volume of 100 mm$^3$ (range 70–130 mm$^3$) at 34 days post implantation, 12 mice were randomized into each of four treatment groups. H460-16-2 or isotype control antibody (known not to bind MB-231 cells) was administered intravenously with 15 mg/kg/dose at a volume of 150 microliters after dilution from the stock concentration with a diluent that contained 2.7 mM KCl, 1 mM $KH_2PO_4$, 137 mM NaCl and 20 mM $Na_2HPO_4$; cisplatin was administered at 9 mg/kg/dose (diluted in saline) intraperitoneally in 300 microliters. The antibodies were then administered 3 times per week for a total of 10 doses in the same fashion until day 48 post-implantation. Cisplatin was administered every four days for 3 doses. Tumor growth was measured around every 7th day with calipers for the duration of the study or until individual animals reached CCAC end-points. Body weights of the animals were recorded for the duration of the study. At the end of the study all animals were euthanised according to CCAC guidelines.

Figure 4:
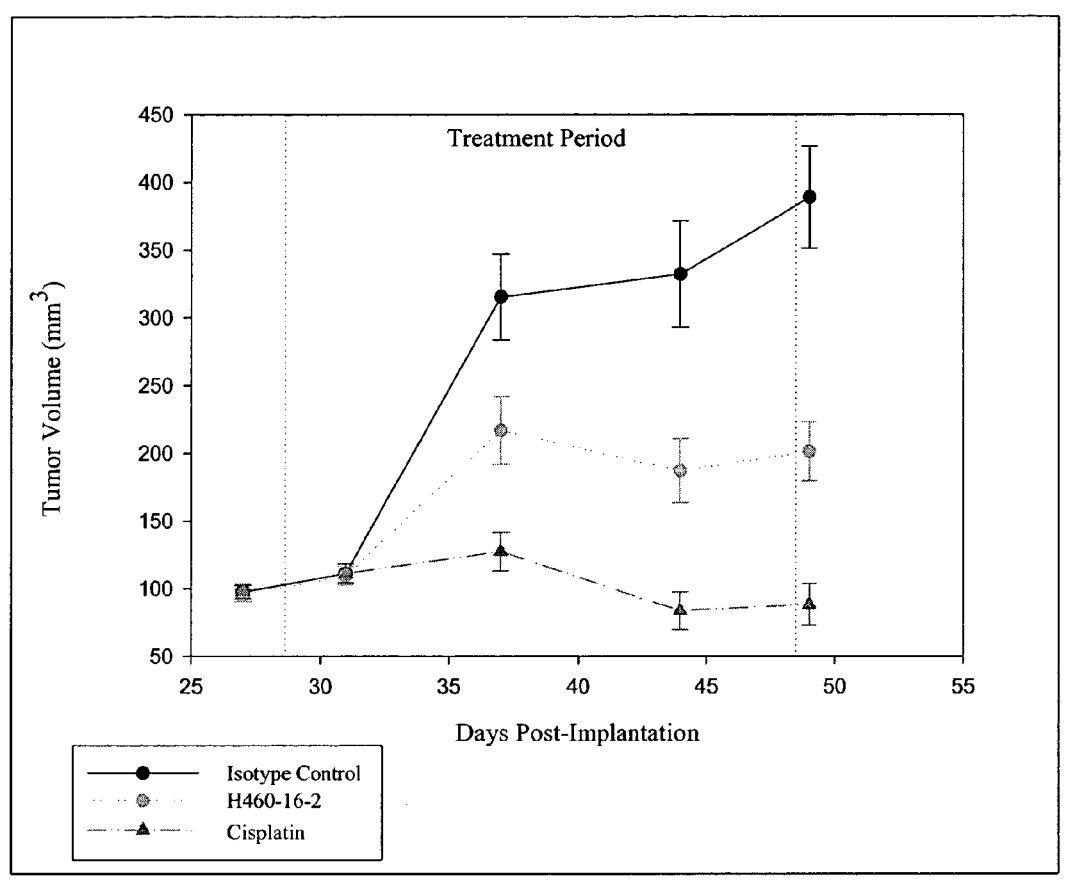
FIG. 4. Effect of H460-16-2 on tumor growth in an established MDA-MB-231 breast cancer model. The dashed line indicates the period during which the antibody was administered. Data points represent the mean+/−SEM.

At the time of randomization the mean tumor volumes and the standard deviations in each group were similar: isotype control, (97.60+/−18.33); H460-16-2 (95.25+/−16.82); cisplatin (98.00+/−18.93). This indicated that true randomization had occurred. As shown in FIG. 4 the antibody H460-16-2 was able to significantly suppress tumor growth at the end of the 3-week treatment period. Comparisons of the mean tumor volume between the 3 groups showed the differences between the groups were highly significant (Table 1).

TABLE 1

Mean Tumor Volume Comparison At End Of Treatment

| Group (1) | Group (2) | Mean Difference (1–2) | Std. Error | Sig. |
|---|---|---|---|---|
| Isotype | H460-16-2 | 187.58* | 41.09 | 0 |
|  | Cisplatin | 300.69* | 43.1 | 0 |
| H460-16-2 | Isotype | 187.58* | 41.09 | 0 |
|  | Cisplatin | 113.12* | 43.1 | 0.012 |
| Cisplatin | Isotype | 300.69* | 43.1 | 0 |
|  | H460-16-2 | 113.12* | 43.1 | 0.012 |

*The mean difference is significant at the 0.05 level.

Figure 5:
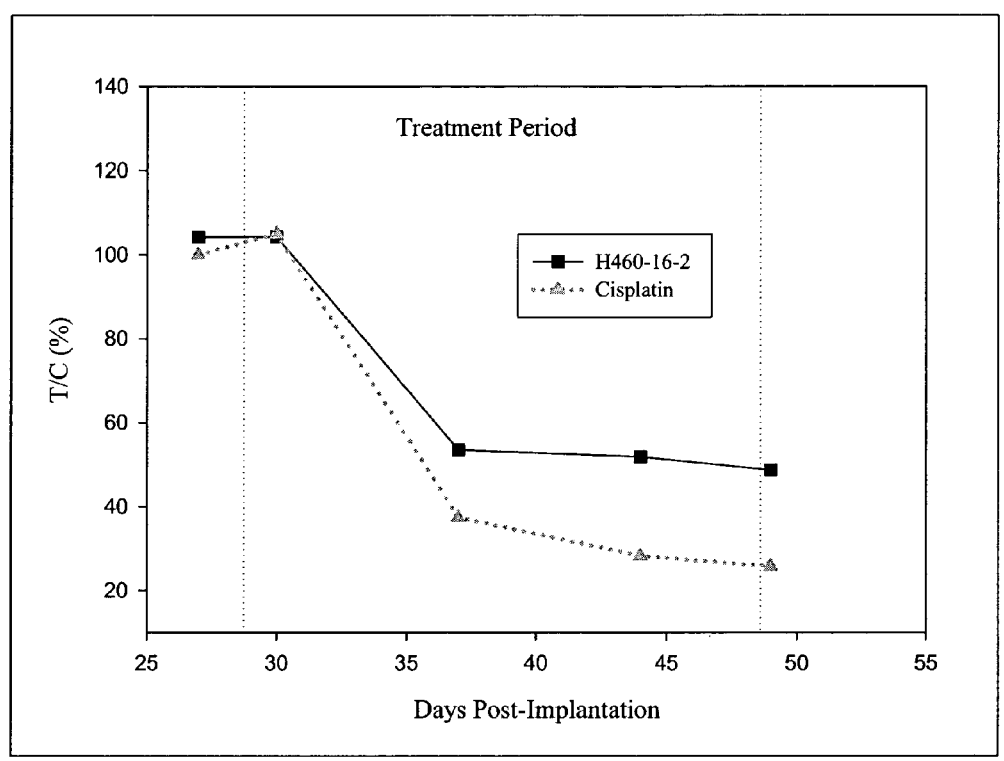
FIG. 5. Graphical representation of treatment efficacy or the anti-tumor effect of ARH460-16-2, and Cisplatin. Growth inhibition was calculated as a ratio of the median tumor volume of treated versus the isotype control treated group in percent: T/C×100, where T is the median tumor of the treated group and C the median tumor volume of the control group on day X. The dashed line indicates period of treatment.
Figure 6:
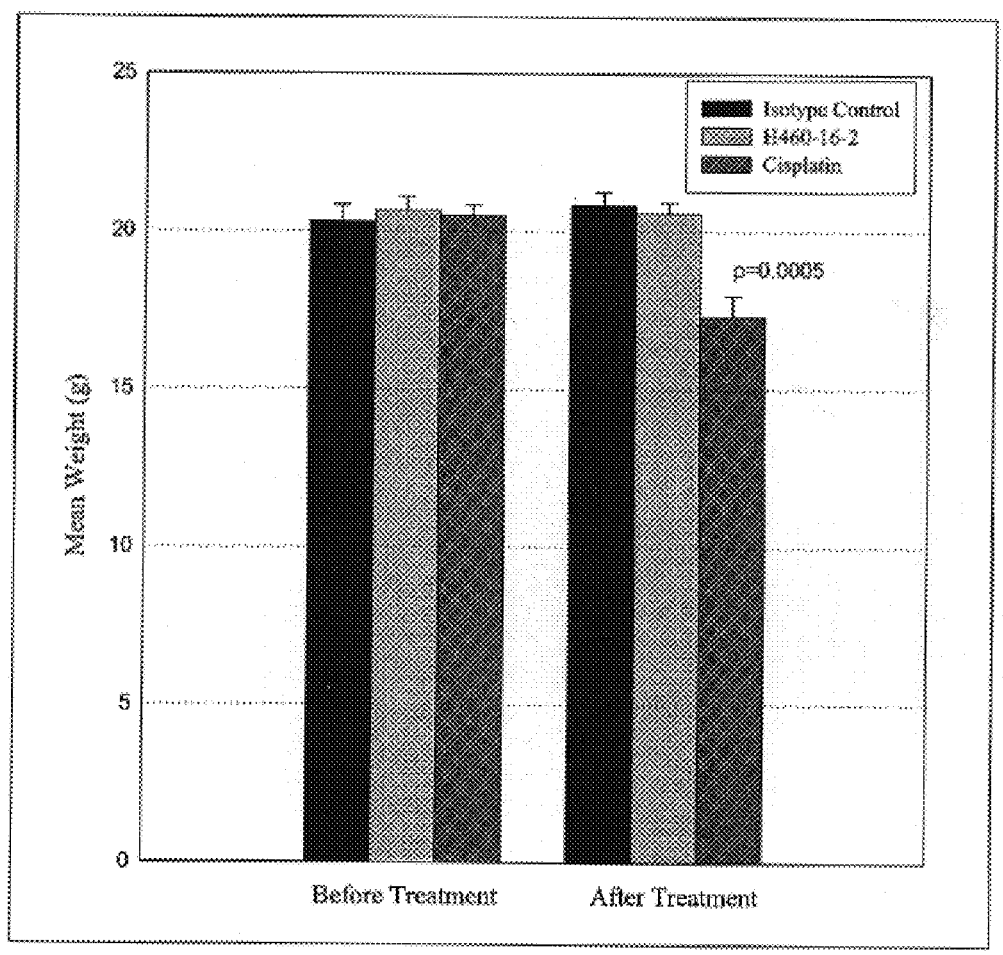
FIG. 6. Mean body weights of the animals in the study groups before and after the treatment period.

Further evaluation of efficacy was assessed by calculating T/C (median tumor volume of treated (T) versus the median tumor volume of isotype control (C) in a percent) ratios which reflect growth inhibition. H460-16-2 antibody achieved an endpoint of median T/C tumor volume equal to 49% (FIG. 5). FIG. 4 further shows that H460-16-2 treatment resulted in marked suppression of tumor growth when compared to the isotype control and that the suppression was ⅔that of cisplatin given at its maximum tolerated dose (MTD) but without cisplatin's accompanying toxicity or death.

Body weights recorded weekly for the duration of the experiment were used as a surrogate for evaluation of safety and toxicity. As outlined in Table 2 and displayed in FIG. 6, there was a minimal difference in weight for the groups treated with the isotype control or H460-16-2. In contrast, during the treatment period, there was significant (p=0.0005) cachexia observed in the cisplatin group. In this group, weight loss reached 19.2% of the initial body weight and additional evidence of clinical distress such as ruffled fur, skin tenting due to dehydration and lethargy occurred. There were no deaths in the H460-16-2 treated group compared to 2 deaths observed in the cisplatin treated group.

TABLE 2

Changes In Body Weight And Tumor Growth Suppression (% T/C) At End Of Treatment

| Therapeutic Agent | No./Group | Dose | % Body Weight Change | % Tumor Growth Suppression |
|---|---|---|---|---|
| Isotype Control | 12 | 15 mg/kg/dose* | no mean |  |
| H460-16-2 | 12 | 15 mg/kg/dose* | −2.30% | 49 |
| Cisplatin | 12 (−2) | 9 mg/kg/dose** | −19.20% | 25 |

*Dose administered i.v. 3 × per week for 3 weeks.
**Dose administered i.p. 1 × every 4 days for 3 doses.

Figure 7:
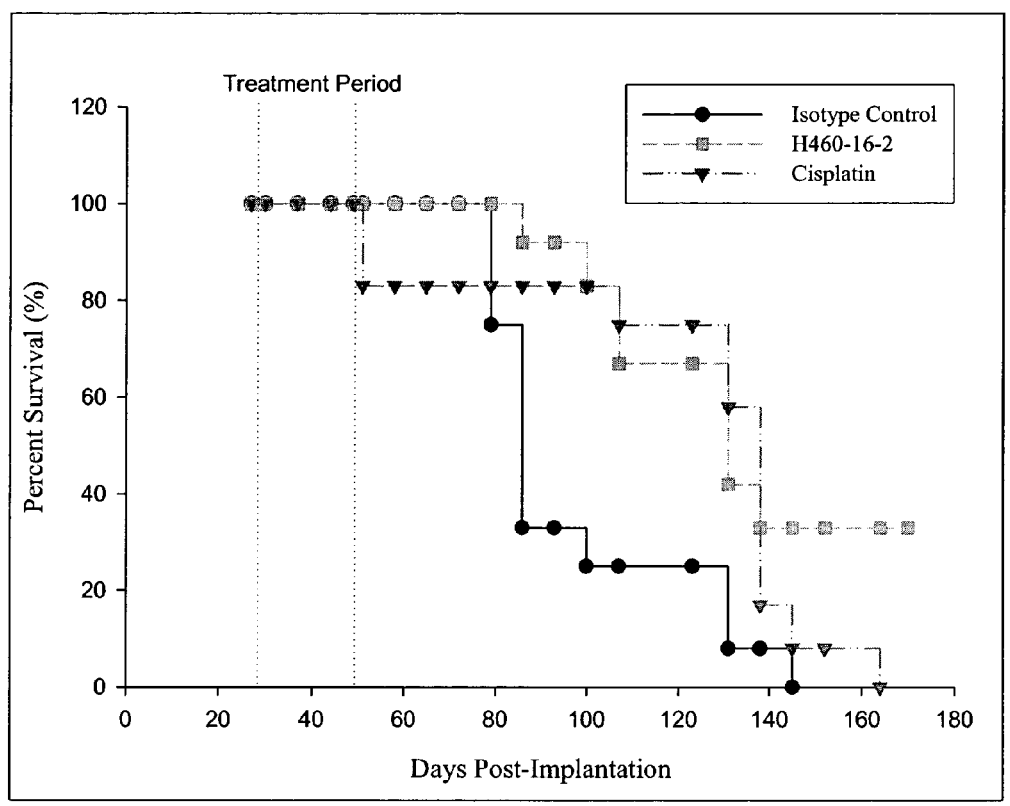
FIG. 7. Survival of tumor-bearing mice after treatment with H460-16-2, Cisplatin or isotype control antibody. Mice were monitored for survival for over 60 days post-treatment.
Figure 8:
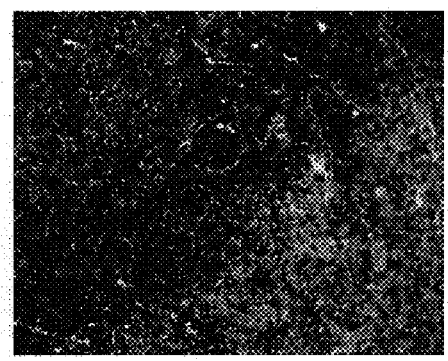
FIG. 8. Human MB-231 Breast Cancer Explanted from a SCID Mouse. A. Anti-vimentin. B. H460-16-2. C. Anti-gp96. Arrow points to cells with cytoplasmic and punctate staining. Magnification is 100×.
Figure 8:
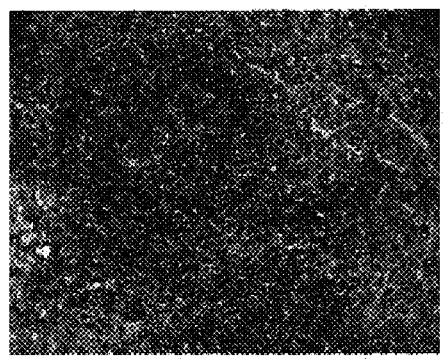
Figure 8:
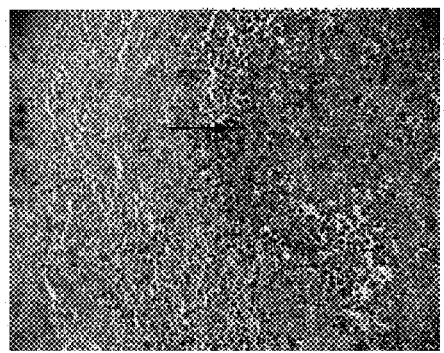

H460-16-2 showed a survival benefit in comparison to treatment with isotype control (FIG. 7). By day 170 (around 120 days post-treatment), 33 percent of the H460-16-2 treatment group was still alive compared to 0 percent for both the cisplatin and isotype control groups.

In summary, H460-16-2 is significantly more effective than the isotype control antibody in suppressing tumor growth in an established tumor xenograft model of breast cancer in SCID mice. Over the 3-week treatment period, H460-16-2 achieved an endpoint of median T/C tumor volumes of less than 50% relative to control. In addition, H460-16-2 resulted in suppression that was two thirds that of cisplatin given at MTD but without the signs of toxicity or death observed with the chemotherapeutic drug.

Therefore treatment with H460-16-2 significantly decreased the tumor burden of established tumors in comparison to a control antibody and showed survival benefits in a well-recognized model of human cancer disease suggesting pharmacologic and pharmaceutical benefits of this antibody for therapy in other mammals, including man.

EXAMPLE 3

Normal Mouse Tissue Staining

The distribution of the H460-16-2 antigen was studied in mouse tissues and compared to the gp96 antigen. IHC optimization studies were initially performed in order to determine the conditions for further experiments. H460-16-2 monoclonal antibody was produced and purified as stated above.

An untreated mouse implanted sub-cutaneously with MB-231 tumor cells was euthanised 74 days post-implantation. Tumor tissue and tissue from major organs were dissected out and fixed in 10% neutral buffered formalin for 48 hours. Following fixation, the tissues were transferred to 70% ethanol, processed, paraffin-embedded, sectioned and mounted on glass slides for staining. Slides were deparaffinized by drying in an oven at 60° C. for 1 hour and dewaxed by immersing in xylene 5 times for 4 minutes each in Coplin jars. Following treatment through a series of graded ethanol washes (100%–75%) the sections were rehydrated in water. The slides were immersed in 10 mM citrate buffer at pH 6 (Dako, Toronto, ON) then microwaved at high, medium, and low power settings for 5 minutes each and finally immersed in cold PBS. Slides were then immersed in 3% hydrogen peroxide solution for 6 minutes, washed with PBS three times for 5 minutes each, dried, incubated with Universal blocking solution (Dako, Toronto, ON) for 5 minutes at room temperature, and dried. H460-16-2, monoclonal mouse anti-vimentin (Dako, Toronto, ON) and anti-grp94, also known as anti-gp96, (Stressgen Biotechnologies, Victoria, BC) were diluted in antibody dilution buffer (Dako, Toronto, ON) to its working concentration (either 2.5μg/mL, 5μg/mL or 10μg/mL for each antibody) and incubated overnight in a humidified chamber at 4° C. The slides were washed with PBS 3 times for 5 minutes each. Immunoreactivity of the primary antibodies was detected/visualized with HRP conjugated secondary antibodies as supplied (Dako Envision System, Toronto, ON) for 30 minutes at room temperature. Following this step the slides were washed with PBS 3 times for 5 minutes each and a color reaction developed by adding DAB (3,3'-diaminobenzidine tetrahydrachloride, Dako, Toronto, ON) chromogen substrate solution for immunoperoxidase staining for 10 minutes at room temperature. Washing the slides in tap water terminated the chromogenic reaction. Following counterstaining with Meyer's Hematoxylin (Sigma Diagnostics, Oakville, ON), the slides were dehyrdated with graded ethanols (75–100%) and cleared with xylene. Using mounting media (Dako Faramount, Toronto, ON) the slides were coverslipped. Slides were microscopically examined using an Axiovert 200 (Zeiss Canada, Toronto, ON) and digital images acquired and stored using Northern Eclipse Imaging Software (Mississauga, ON). Results were read, scored and interpreted by a pathologist.

The optimum concentration was the one that produced the expected results for the positive (anti-gp96) and negative control antibodies (anti-vimentin). The anti-vimentin antibody has been shown to be negative on mouse tissue but positive on human tissue. The anti-gp96 antibody has previously been shown to be positive on both mouse and human tissue. In these studies both the high and low concentrations did not produce the expected results with the control antibodies, but the 5 μg/mL concentration did.

TABLE 3

IHC Of Engrafted MB-231 and SCID Mouse Tissue

| Tissue | Anti-vimentin | H460-16-2 | Anti-gp96 |
|---|---|---|---|
| MB-231 | +++<br>MB-231 (M/C) | +++<br>MB-231 (M) | ++<br>MB-231 (C/P) |
| Liver | – | – | +++<br>hepatocytes (C) |
| Pancreas | – | – | ++<br>Islets of<br>Langerhans (C/P) |
| Spleen | – | – | – |
| Heart | – | – | – |
| Adipose Tissue | – | – | – |
| Lung | +++<br>Metastatic<br>MB-231 (C) | +<br>Metastatic<br>MB-231 (M) | +<br>Metastatic<br>MB-231 (C) |

TABLE 3-continued

IHC Of Engrafted MB-231 and SCID Mouse Tissue

| Tissue | Anti-vimentin | H460-16-2 | Anti-gp96 |
|---|---|---|---|
| Kidney | – | +++<br>DCT + PCT (A) | ++<br>DCT + PCT (C/D/P) |
| Brain | – | – | +<br>Astrocytes (C/P)<br>(Cerebrum) |
| Ovary | – | ++<br>Ova (C/N) | +++<br>Zona Granulosa (C/P)<br>Ova (C/N/D) |
| Fallopian Tubes | – | – | ++<br>Mucosal<br>epithelium (C/A) |

Abbreviations are-
M: Membrane staining;
C: Cytoplasmic staining;
M/C: Membrane-cytoplasmic staining;
N: Nuclear staining;
D: Diffuse staining;
P: Punctate staining;
A: Apical staining;
DCT: Distal convoluted tubule;
PCT: Proximal convoluted tubule.

The results of an IHC survey of SCID mouse tissue and engrafted human breast cancer, MB-231 (Table 3) shows the negative control antibody anti-vimentin is negative for mouse tissue but positive for human tissue. Anti-vimentin (FIG. 8A) shows intense cytoplasmic and some membranous staining; H460-16-2 shows intense membranous staining (FIG. 8B), and anti-gp96 shows occasional positive punctate and cytoplasmic staining cells (FIG. 8C). Anti-vimentin (FIG. 9A) and H460-16-2 (FIG. 9B) did not stain mouse liver but anti-gp96 produced intense cytoplasmic staining of hepatocytes (FIG. 9C). Anti-vimentin (FIG. 10A) did not stain mouse kidney. H460-16-2 (FIG. 10B) showed apical staining of the proximal and distal convoluted tubules while anti-gp96 produced diffuse staining of the same cells with a cytoplasmic and punctate pattern (FIG. 10C). Anti-vimentin (FIG. 11A) did not stain mouse ovary. H460-16-2 (FIG. 11B) showed cytoplasmic and nuclear staining of only the ova while anti-gp96 produced diffuse cytoplasmic and nuclear staining of the ova and cytoplasmic and punctate staining of granulosa cells (FIG. 11C).

The anti-vimentin negative control antibody gave the expected staining of human tissues and lack of staining of mouse tissues (see FIGS. 8–11). The anti-gp96 antibody was used as a positive control because of the likelihood that the H460-16-2 antigen is a cancer variant of gp96. The anti-gp96 antibody did show staining of MB-231 cells (FIG. 8) which is consistent with the association of gp96 expression with breast cancer. Gp96 was also expressed in the cytoplasm of many cell types involved with protein synthesis such as hepatocytes, cells of the Islets of Langerhans in the pancreas, ovarian granulosa cells and the ova, and mucosal epithelium in the fallopian tubes (Table 3). This is entirely consistent with the putative role for gp96 as an endoplasmic reticular chaperone protein.

Figure 9:
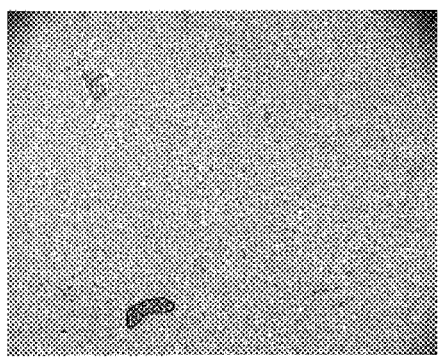
FIG. 9. Mouse Liver. A. Anti-vimentin. B. H460-16-2. C. Anti-gp96. Note positive staining by anti-gp96 of hepatocytes. Magnification is 100×.
Figure 9:
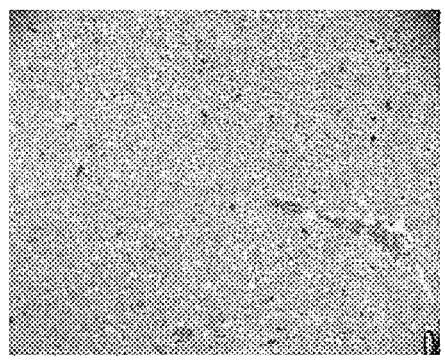
Figure 9:
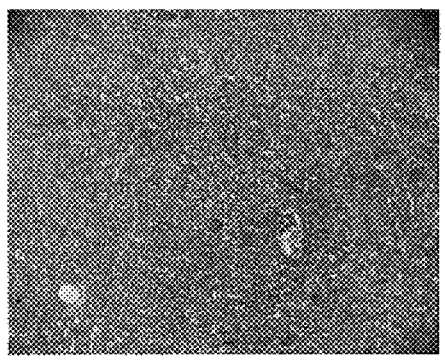
Figure 10:
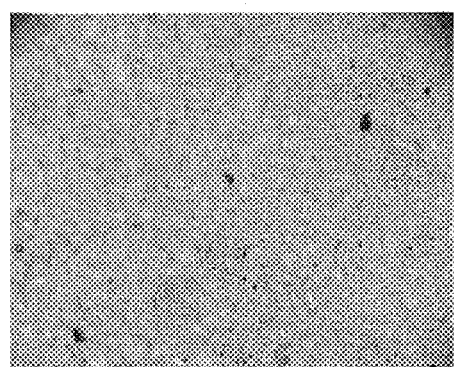
FIG. 10. Mouse Kidney A. Anti-vimentin. B. H460-16-2. Arrow points to apical staining of tubular cells. C. Anti-gp96. Arrow points to diffuse staining of tubular cells. Magnification is 100×.
Figure 10:
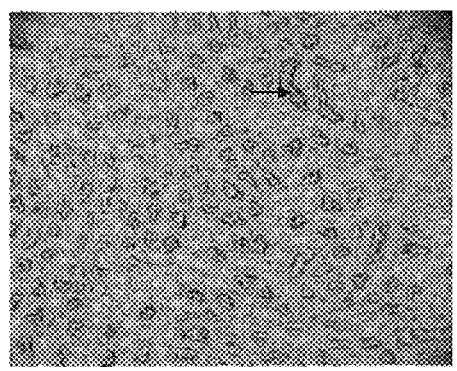
Figure 10:
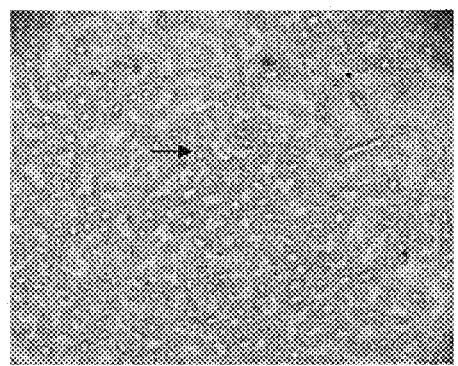
Figure 11:
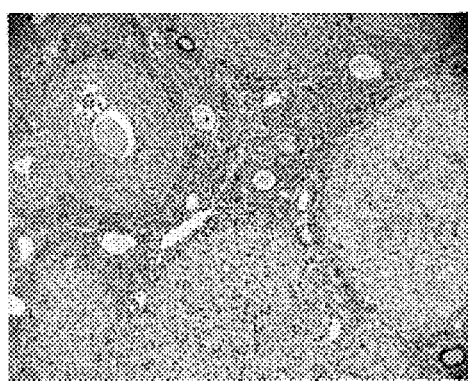
FIG. 11. Mouse Ovary A. Anti-vimentin. B. H460-16-2. Arrow points to cyoplasmic staining of ova in the follicle. C. Anti-gp96. Arrow points to granulosa cells. Magnification is 100×.
Figure 11:
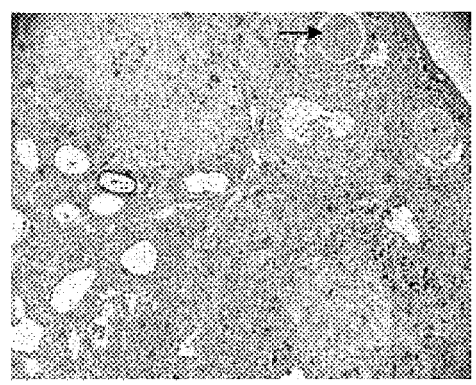
Figure 11:
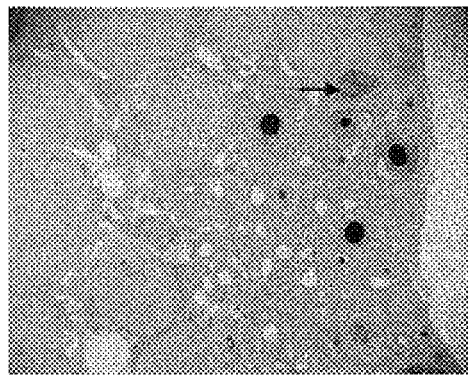

H460-16-2 antibody stained MB-231 cells which is consistent with its in vivo effects in the corresponding tumor model. In addition it stained the DCT and PCT in the mouse kidney (Table 3) as well as the mouse ova (FIG. 11). From this sampling of mouse tissues it would appear that the H460-16-2 antigen is not restricted to just human cells but is also expressed in the mouse in such a way that the antibody can recognize the antigen. Significantly there are differences in the expression of the H460-16-2 and gp96 antigen as demonstrated with the staining of normal mouse kidney tissue; apical staining was obtained with H460-16-2 while diffuse staining was seen with anti-gp96 (FIG. 10). Another example of this is the additional staining of the ova with anti-gp96 (FIG. 11). A key difference is that H460-16-2 staining does not occur in the liver, while gp96 staining is quite extensive (FIG. 9).

In order to further the experiments described above, H460-16-2, anti-gp96 (for comparison to H460-16-2) and anti-vimentin (negative control) was used to stain a normal mouse tissue array (Imgenex, San Diego, CA). The staining procedure used was the same as stated above. As summarized in Table 4, anti-vimentin did not stain any of the tissues tested; H460-16-2 again stained only the ovary and kidney while anti-gp96 continued to stain a much broader range of mouse tissues. These results are consistent with those stated above and again demonstrates that H460-16-2 expression is not limited to human cells and that its expression is restricted and specific on normal mouse tissue. It also confirms that H460-16-2 stains the same tissues as anti-gp96 but anti-gp96 continued to stain a much broader range of tissues supporting the idea that the H460-16-2 antigen may be a subset of gp96.

TABLE 4

IHC on Normal Mouse Tissue Array

| Tissue | Anti-vimentin | H460-16-2 | Anti-gp96 |
|---|---|---|---|
| 1 Skin | – | – | – |
| 2 Skin | – | – | – |
| 3 Spleen | – | – | +/–(Lymphocytes) |
| 4 Spleen | – | +/–(Lymphocytes) | +/–(Lymphocytes) |
| 5 Skeletal Muscle | – | – | – |
| 6 Lung | – | – | – |
| 7 Lung | – | – | – |
| 8 Heart | – | – | – |
| 9 Heart | – | – | – |
| 10 Salivary gland | – | – | +/–(Acinar epith.) |
| 11 Liver | – | – | ++(Hepatocytes) |
| 12 Liver | – | – | ++(Hepatocytes) |
| 13 Gall bladder | –(NR) | –(NR) | –(NR) |
| 14 Pancreas | – | – | +(Acinar epith.) |
| 15 Esophagus | – | – | +(Ganglion cells.) |
| 16 Stomach | – | – | ++(Gastric gland epith.) |
| 17 Stomach | – | – | ++(Gastric gland epith.) |
| 18 Small bowel | – | – | ++(Mucosal epith. & lymphocytes/macrophages) |
| 19 Small bowel | – | – | ++(Mucosal epith. & lymphocytes/macrophages in lamina propria) |
| 20 Colon | – | – | ++(Mucosal epith. & lymphocytes/macrophages in lamina propria) |
| 21 Colon | – | – | ++(Mucosal epith. & lymphocytes/macrophages in lamina propria) |
| 22 Kidney | – | ++(Tubular epith) | ++(Tubular epith) |
| 23 Kidney | – | +++(Tubular epith) | ++(Tubular epith) |
| 24 Uterus | – | – | – |
| 25 Uterus | – | – | +++(Endometrial mucosal epith. & glands) |
| 26 Ovary | – | +(ova) | +++(Ova & zona granulosa) |
| 27 Adrenal | – | – | ++(Endocrine cells) |
| 28 Thymus | –(NR) | –(NR) | –(NR) |
| 29 Brain | – | – | – |
| 30 Brain | – | – | – |
| 31 Small bowel | – | – | – |

Abbreviations:
NR: Non-representative photo.

EXAMPLE 4

Normal Human Tissue Staining

IHC studies were conducted to characterize H460-16-2 antigen distribution in humans. It was compared to an antibody directed against gp96 since the H460-16-2 antigen may be a cancer variant of gp96 as determined previously by biochemical methods. Binding of antibodies to 60 normal human tissues was performed using a human, normal organ tissue array (Imgenex, San Diego, Calif.). All primary antibodies (H460-16-2; anti-grp94 (also known as anti-gp96, Stressgen Biotechnologies, Victoria, BC); and mouse IgG$_1$ negative control (Dako, Toronto, ON)) were diluted in antibody dilution buffer (Dako, Toronto, ON) to a concentration of 5 µg/ml (found to be the optimal concentration in optimization steps). The negative control antibody has been shown to be negative to all mammalian tissues by the manufacturer. The procedure for IHC from Example 3 was followed.

Table 5 presents a summary of the results of H460-16-2 staining to an array of normal human tissues. From the table, there are three categories of tissue staining. A group of tissues was completely negative. These tissues included normal heart, kidney, brain, pancreas, breast, testis, ovary and placenta. A second group of tissues comprised tissues that demonstrated positive staining. These included the skin, ureter, stomach and prostate. The salivary gland demonstrated the strongest staining with this antibody. A third group of tissues included tissues in which staining was positive in the tissue section, but was limited to infiltrating macrophages, lymphocytes and fibroblasts. This included macrophages in the lung, liver, stomach, intestine and colon, as well as lymphocytes in the spleen and gall bladder. It should be noted that the antigen is not present on cells in the vital organs, including liver, kidney, heart and lung. The antibody does bind to macrophages and lymphocytes, and their presence is observed in some of the organs in these sections. In comparison, tissues that were negative for anti-gp96 included subcutaneous fat, skeletal muscle, lung, heart, stomach smooth muscle, urinary bladder, myometrium, ovary, placental cord, brain (white and gray matter), cerebellum, and spinal cord. With the exception of the myometrium, all of these tissues were also negative for H460-16-2 staining. These results suggest that H460-16-2 binds to a smaller subset of the tissues recognized by the anti-gp96 antibody. This is consistent with the mouse tissue study, in which anti-gp96 bound to liver, pancreas, brain and fallopian tubes in addition to the two tissues that were also bound by H460-16-2, kidney and ovary. These results suggest that the antigen for H460-16-2 is not widely expressed on normal tissues, and that the antibody would bind specifically to a limited number of tissues in humans.

TABLE 5

IHC On Normal Human Tissue With H460-16-2

| | Negative | Negative except Macrophages, Lymphocytes, Fibroblasts | Positive |
|---|---|---|---|
| 1. | breast | subcutaneous fat | skin, buttock |
| 2. | skeletal muscle | spleen | salivary gland |
| 3. | bronchus | lymph node, mesenteric | stomach, antrum |
| 4. | heart | nasal mucosa | prostate |
| 5. | pancreas | lung | seminal vesicle |
| 6. | stomach smooth muscle | liver | endometrium, secretory |
| 7. | kidney cortex | gallbladder | thyroid |
| 8. | kidney medulla | tonsil | ureter |
| 9. | testis | esophagus | myometrium |
| 10. | epidydimis | stomach, body | |
| 11. | endometrium, proliferative | duodenum | |
| 12. | ovary | ileum | |
| 13. | placenta, villi | appendix | |
| 14. | placenta, amniochorion | colon | |
| 15. | placenta cord | sigmoid colon | |
| 16. | adrenal cortex | urinary bladder | |
| 17. | adrenal medulla | uterine cervix (endocervix) | |
| 18. | thymus | uterine cervix (exocervix) | |
| 19. | brain, white matter | salpinx | |
| 20. | brain, gray matter | | |
| 21. | cerebellum | | |
| 22. | spinal cord | | |

To delineate the differences between the distribution of gp96 and the H460-16-2 antigen, the cell types where the antigens are expressed were tabulated in Table 6. From the table, it is clear that the anti-gp96 antibody binds to a wider range of cell types than H460-16-2. Further, the strongest binding of H460-16-2 was to fibroblasts, acinar epithelium, and lymphocytes. There was weak binding to macrophages, keratinocytes, smooth muscle, mucosal epithelium, and thyroid follicular cells. Anti-gp96 bound to an additional 15 cell types, and to each cell type that expressed the H460-16-2 antigen. This suggests that the H460-16-2 antigen is a subset of gp96 since there were no cells that expressed H460-16-2 that did not express the gp96 antigen.

TABLE 6

Summary Of IHC on Normal Human Tissues

| Cell Type | H460-16-2 | Anti-gp96 |
|---|---|---|
| Fibroblasts | +/++ | + |
| Acinar epithelium | +/++++ | + |
| Lymphocytes | +/++ | +/++ |
| Macrophages | + | + |
| Keratinocytes | + | + |
| Smooth muscle | + | + |
| Mucosal epithelium | + | + |
| Follicular cells | + | + |
| Lobular epithelium | − | + |
| Endothelium | − | + |
| Mucosal glands | − | + |
| Ductal epithelium | − | + |
| Hepatocytes | − | ++ |
| Acinar cells | − | ++ |
| Ganglionic cells | − | + |
| Villous epithelium | − | + |
| Loops of Henle | − | + |
| PCT & DCT | − | +/++ |
| Glandular epithelium | − | +/++/+++ |
| Germinal cells | − | ++ |
| Cytotrophoblasts | − | ++ |
| Syncytiotrophoblasts | − | ++ |
| Granulosa cells | − | + |

These tissue surveys demonstrated that the H460-16-2 antigen has a very limited distribution in normal tissues including the vital organs. The experiment also showed that the anti-gp96 antibody bound to a wider range of tissues compared to H460-16-2. H460-16-2 binds to a subset of the tissues bound by anti-gp96 and to limited cell types. In the tissues that were H460-16-2 positive but not gp96 positive, H460-16-2 bound to only macrophages and fibroblasts, cell types which generally expressed gp96. The difference between the mouse and human tissue surveys also point out that the H460-16-2 antibody recognizes an antigen that is relevant in humans and of limited importance in normal mice since the expression is so limited. The H460-16-2 antibody itself is applicable in humans since it does recognize the human form of the antigen.

EXAMPLE 5

Human Tumor Tissue Staining

An IHC study was undertaken to determine the cancer association of the H460-16-2 antigen with human breast cancers and whether the H460-16-2 antibody was likely to recognize human cancers. A comparison was made for anti-gp96 staining, and an antibody directed towards *Aspergillus niger* glucose oxidase, an enzyme which is neither present nor inducible in mammalian tissues (negative control). A breast cancer tissue array derived from 50 breast cancer patients and 9 samples derived from non-neoplastic breast tissue in breast cancer patients was used (Imgenex Corporation, San Diego, Calif.). The following information was provided for each patient: age, sex, American Joint Committee on Cancer (AJCC) tumor stage, lymph node, estrogen receptor (ER) and projesterone receptor (PR) status. The procedure for IHC from Example 3 was followed. All antibodies were used at a working concentration of 5 µg/ml.

Figure 12:
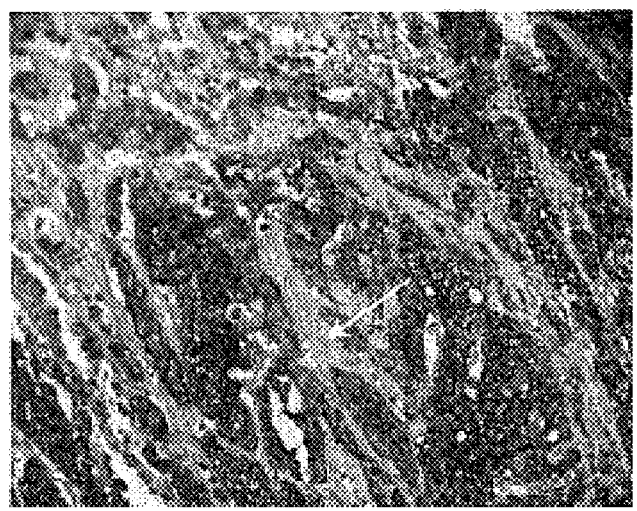
FIG. 12. Representative micrograph of H460-16-2 binding to breast cancer tumor (infiltrating duct carcinoma). The yellow and orange arrows in panel point to stromal cells and sheets of malignant cells respectively. Magnification is 100×.
Figure 13:
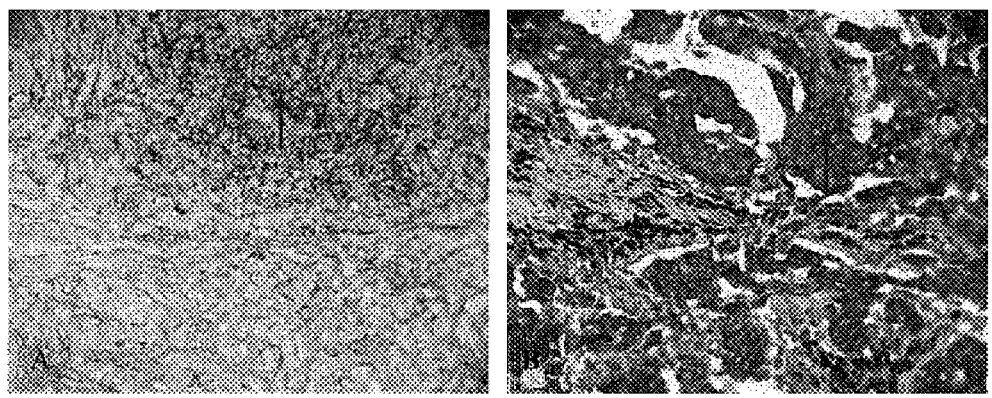
FIG. 13. Representative micrographs showing the binding pattern obtained with H460-16-2 (A) and the anti-gp96 antibody (B) on tissues sections of infiltrating duct carcinoma samples from a breast cancer tissue array. Blue arrows indicate cellular localization of the antigenic target. Magnification is 200×.

Tables 7 and 8 provide binding summaries of H460-16-2 and anti-gp96 antibody to a breast cancer tissue array respectively. Each array contained tumor samples from 50 individual patients. Overall, 64 percent of the 50 patients tested were positive for H460-16-2 antigen compared to 84 percent for gp96. For both the H460-16-2 and gp96 antigen, only 2 out of normal breast tissue samples from breast cancer patients were positive. No clear correlation between estrogen and progesterone receptor status was evident. It also appeared there was a trend to greater positive expression of the H460-16-2 antigen with higher tumor stage. The H460-16-2 staining was quite specific for cancerous cells over normal cells as demonstrated in FIG. 12 where stromal cells were clearly negative and sheets of malignant cells were highly positive. The cellular localization pattern seen with the H460-16-2 antigen was confined to the cell membrane in the majority of cases. The anti-gp96 antibody stained more breast cancer samples but consistently showed membrane as well as substantial cytoplasmic localization (FIG. 13). Anti-gp96 stained the same samples of normal tissue from breast cancer patients as H460-16-2. These results suggest the antigen for H460-16-2 may be expressed by almost two thirds of breast cancer patients. The staining pattern showed that in patient samples, the antibody is highly specific for malignant cells and the H460-16-2 antigen is localized to the cell membrane thereby making it an attractive druggable target.

TABLE 7

IHC With H460-16-2 On Human Normal Breast And Tumor

| H460-16-2 | | Total # | − | +/− | + | ++ | +++ | Total positive | % positive |
|---|---|---|---|---|---|---|---|---|---|
| Patient | Tumor | 50 | 18 | 13 | 15 | 2 | 2 | 32 | 64 |
| Samples | Normal | 9 | 7 | 0 | 2 | 0 | 0 | 2 | 22 |
| ER | ER+ | 21 | 9 | 5 | 7 | 0 | 0 | 12 | 57 |
| Status | ER− | 28 | 8 | 8 | 8 | 2 | 2 | 20 | 71 |
| | Unknown | 1 | 1 | 0 | 0 | 0 | 0 | 0 | 0 |
| PR | PR+ | 11 | 5 | 2 | 4 | 0 | 0 | 6 | 55 |
| Status | PR− | 38 | 12 | 11 | 11 | 2 | 2 | 26 | 68 |
| | Unknown | 1 | 1 | 0 | 0 | 0 | 0 | 0 | 0 |
| AJCC | T1 | 7 | 3 | 2 | 2 | 0 | 0 | 4 | 57 |
| Tumor | T2 | 26 | 11 | 5 | 6 | 2 | 2 | 15 | 58 |
| Stage | T3 | 16 | 4 | 6 | 6 | 0 | 0 | 12 | 75 |
| | T4 | 1 | 0 | 0 | 1 | 0 | 0 | 1 | 100 |

TABLE 8

IHC With H4Anti-gp96 On Human Breast Normal And Tumor

| Anti-gp96 | | Total # | − | +/− | + | ++ | +++ | Total positive | % positive |
|---|---|---|---|---|---|---|---|---|---|
| Patient | Tumor | 50 | 8 | 9 | 12 | 9 | 12 | 42 | 84 |
| Samples | Normal | 9 | 7 | 0 | 1 | 1 | 0 | 2 | 22 |
| ER | ER+ | 21 | 6 | 5 | 4 | 3 | 3 | 15 | 71 |
| Status | ER− | 28 | 1 | 4 | 8 | 6 | 9 | 27 | 96 |
| | Unknown | 1 | 1 | 0 | 0 | 0 | 0 | 0 | 0 |
| PR | PR+ | 11 | 4 | 1 | 2 | 2 | 2 | 7 | 64 |
| Status | PR− | 38 | 3 | 8 | 10 | 7 | 10 | 35 | 92 |
| | Unknown | 1 | 1 | 0 | 0 | 0 | 0 | 0 | 0 |
| AJCC | T1 | 7 | 2 | 2 | 0 | 3 | 0 | 5 | 71 |
| Tumor | T2 | 26 | 5 | 5 | 5 | 5 | 6 | 21 | 81 |
| Stage | T3 | 16 | 1 | 2 | 6 | 1 | 6 | 15 | 94 |
| | T4 | 1 | 0 | 0 | 1 | 0 | 0 | 1 | 100 |

To determine whether the H460-16-2 antigen is expressed on other human tumor tissues besides breast, H460-16-2 was used on a multiple human tumor tissue array (Ihgenex, San Diego, Calif.). The following information was provided for each patient: age, sex, organ and diagnosis. The staining procedure used was the same as the one outlined in Example 3. Vimentin was used as a positive control antibody and the same negative control antibody was used as described for the human breast tumor tissue array. All antibodies were used at a working concentration of 5 μg/mL.

As outlined in Table 9, H460-16-2 stained a number of various human cancers besides breast. The following tumor types were always positive for H460-16-2 (albeit to different degrees): lymph node (2/2), bone (2/2), lung (4/4), kidney (3/3), uterus (3/3), and thyroid (2/2). The stomach (4/5), liver (2/3) and partied gland (2/3) also showed up relatively consistently positive for staining. Several other tumor types also occasionally stained positive. As seen with the breast cancers, H460-16-2 staining was localized predominately on the membrane of cancerous cells.

Therefore, it appears that the H460-16-2 antigen is not solely found on the membranes of breast cancers but also on the membrane of a large variety of tumor types. These results indicate that H460-16-2 has potential as a therapeutic drug in a wide variety of tumor types besides breast.

TABLE 9

IHC On Human Multi-Tumor Array

| Sec. No. | Age | Sex | Organ | Diagnosis | H460-16-2 | Vimentin | Negative Control |
|---|---|---|---|---|---|---|---|
| 1 | 59 | M | Skin | Malignant melanoma | +++ M | +++ M/C | − |
| 2 | 25 | F | Skin | Squamous cell carcinoma | − | +++ M/C | − |
| 3 | 50 | F | Breast | Infiltrating ductal carcinoma | + Tumor, +++ Stroma | ++ Stroma | − |
| 4 | 57 | F | Breast | Invasive papillary carcinoma | +/− | ++ Stromal fibroblasts, Blood vessels | − |
| 5 | 35 | F | Breast | Infiltrating lobular carcinoma | +/− | CS | − |
| 6 | 40 | M | Lymph node | Malignant lymphoma, immunoplastic | +++ M | +++ M/C | − |
| 7 | 58 | M | Lymph node | Metastatic adenoca from stomach | +/− | +++ Tumor, Lipocytes | − |
| 8 | 53 | F | Bone | Osteosarcoma | + M/C | +++ M/C | − |
| 9 | 26 | M | Bone | Giant cell tumor | + M/C | ++ M/C | − |
| 10 | 40 | M | Bone | Chondrosarcoma | CS | CS | CS |
| 11 | 51 | F | Soft tissue | Liposarcoma | − | +++ M/C | − |
| 12 | 47 | F | Soft tissue | Neurofibromatosis | + M/C | +++ M/C | − |
| 13 | 74 | M | Nasal cavity | Inverted papilloma | ++ M | + Keratin | − |
| 14 | 57 | M | Larynx | Squamous cell carcinoma | +++ M | +++ Stroma | − |
| 15 | 60 | M | Lung | Adenocarcinoma | +/− | ++ M/C | − |
| 16 | 51 | F | Lung | Squamous cell carcinoma | +++ M/C | +++ M/C | − |
| 17 | 68 | F | Lung | Adenocarcinoma | +/− | +++ M/C | − |
| 18 | 60 | M | Lung | Small cell carcinoma | +/− | +++ M/C | − |
| 19 | 88 | F | Tongue | Squamous cell carcinoma | +++ M | +++ Stroma | − |
| 20 | 34 | F | Parotid gland | Pleomorphic adenoma | − | ++ M/C | − |
| 21 | 50 | F | Parotid gland | Warthin tumor | +++ M/C | +++ Tumor, Lympho-cytes | − |
| 22 | 40 | F | Parotid gland | Pleomorphic adenoma | ++ M/C | +++ M/C | − |
| 23 | 56 | M | Submandibular gland | Salivary duct carcinoma | − | +++ M/C | − |

TABLE 9-continued

IHC On Human Multi-Tumor Array

| Sec. No. | Age | Sex | Organ | Diagnosis | H460-16-2 | Vimentin | Negative Control |
|---|---|---|---|---|---|---|---|
| 24 | 69 | F | Liver | Cholangiocarcinoma | +/− | +/− Tumor, +++ Blood vessels | − |
| 25 | 51 | M | Liver | Metastatic gastric carcinoma | − | ++ Stroma | − |
| 26 | 64 | M | Liver | Hepatocellular carcinoma | +/− | +/− | − |
| 27 | 62 | F | Gall bladder | Adenocarcinoma | ++ Tumor, Lympocytes | + Stroma | − |
| 28 | 64 | F | Pancreas | Adenocarcinoma | ++ M/C | ++ Stroma | − |
| 29 | 68 | M | Esophagus | Squamous cell carcinoma | +/− | ++ Stroma | − |
| 30 | 73 | M | Stomach | Adenocarcinoma, poorly differentiated | + M/C | ++ Stroma, Blood vessels | − |
| 31 | 63 | M | Stomach | Adenocarcinoma, moderately differentiated | ++ M/C | ++ M/C | − |
| 32 | 59 | F | Stomach | Signet ring cell carcinoma | ++ M/C | ++ M/C | − |
| 33 | 62 | M | Stomach | Malignant lymphoma | +++ M/C | +++ M/C | − |
| 34 | 51 | M | Stomach | Borderline stromal tumor | − | ++ M/C | − |
| 35 | 42 | M | Small intestine | Malignant stromal tumor | − | +++ M/C | − |
| 36 | 52 | F | Appendix | Pseuomyxoma peritonia | − | + Tumor, +++ Lipocytes | − |
| 37 | 53 | M | Colon | Adenocarcinoma | + M/C | ++ Stroma | − |
| 38 | 67 | M | Rectum | Adenocarcinoma | ++ M | ++ Lipocytes, Blood vessels | − |
| 39 | 75 | F | Kidney | Transitional cell carcinoma | + M/C | ++ Stroma | − |
| 40 | 54 | F | Kidney | Renal cell carcinoma | +/− | ++ M | − |
| 41 | 75 | F | Kidney | Renal cell carcinoma | +/− | + Tumor, +++ Stroma | − |
| 42 | 65 | M | Urinary bladder | Carcinoma, poorly differentiated | ++ M/C | ++ Stroma | − |
| 43 | 67 | M | Urinary bladder | Transitional cell carcinoma, high grade | − | +++ Stroma, Blood vessels | − |
| 44 | 62 | M | Prostate | Adenocarcinoma | +++ M | +++ Tumor, Stroma, Blood vessels | − |
| 45 | 30 | M | Testis | Seminoma | +/− | +++ Blood vessels | − |
| 46 | 68 | F | Uterus | Endometrial adenocarcinoma | ++ Stroma | + Tumor, +++ Stroma | − |
| 47 | 57 | F | Uterus | Leimyosacoma | + PS | + M/C | − |
| 48 | 45 | F | Uterus | Leiomyoma | + C | +++ M/C | − |
| 49 | 63 | F | Uterine cervix | Squamous cell carcinoma | +++ M | +/− Tumor, ++ Stroma | − |
| 50 | 12 | F | Ovary | Endodermal sinus tumor | − | ++ Tumor, Stroma | − |
| 51 | 33 | F | Ovary | Mucinous adenocarcinoma | − | ++ Stroma | − |
| 52 | 70 | F | Ovary | Fibrothecoma | − | +++ M/C | − |
| 53 | 67 | F | Adrenal gland | Cortical carcinoma | − | +++ M/C | − |
| 54 | 61 | F | Adrenal gland | Pheohromcytoma | − | +++ M/C | − |
| 55 | 54 | M | Thyroid | Papillary carcinoma | ++ M/C | +/− Tumor, ++ Stroma | − |
| 56 | 58 | F | Thyroid | Follicular carcinoma, minimally invasive | ++ M | +++ M/C | − |
| 57 | 74 | M | Thymus | Thymoma | +/− | ++ M/C | − |
| 58 | 66 | F | Brain | Meningioma | − | +++ M/C | − |
| 59 | 62 | M | Brain | Glioblastoma multiforme | +++ M | ++ Tumor, Blood vessels | − |

Abbreviations: M: Membrane staining; C: Cytoplasmic staining; M/C: Membrane-cytoplasmic staining; CS: The Section is completely sloughed; PS: The section is partially sloughed; F: The section is folded.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification. One skilled in the art will readily appreciate that the present invention is well adapted to carry out the objects and obtain the ends and advantages mentioned, as well as those inherent therein. Any oligonucleotides, peptides, polypeptides, biologically related compounds, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A method of treating a breast tumor in a mammal, wherein said breast tumor expresses an antigen which specifically binds to the isolated monoclonal antibody produced by the hybridoma deposited with the ATCC as accession number PTA-4621, or an antigen binding fragment produced from said isolated antibody, comprising administering to said mammal said isolated monoclonal antibody or said antigen binding fragment in an amount effective to reduce said mammal's tumor burden.

2. The method of claim 1 wherein said isolated monoclonal antibody or antigen binding fragment is conjugated to a cytotoxic moiety.

3. The method of claim 2 wherein said cytotoxic moiety is a radioactive isotope.

4. The method of claim 1 wherein said isolated monoclonal antibody activates complement.

5. The method of claim 1 wherein said isolated monoclonal antibody mediates antibody dependent cellular cytotoxicity.

6. The method of claim 1 wherein the antibody administered is a humanized antibody of the isolated monoclonal antibody produced by the hybridoma deposited with the ATCC under Accession Number PTA-4621, or is an antigen binding fragment of said humanized antibody.

7. The method of claim 1 wherein the antibody administered is a chimeric antibody of the isolated monoclonal antibody produced by the hybridoma deposited with the ATCC under Accession Number PTA-4621, or is an antigen binding fragment of said chimeric antibody.

8. The isolated monoclonal antibody produced by the hybridoma deposited with the ATCC under Accession Number PTA-4621, or an antigen binding fragment produced from said isolated monoclonal antibody.

9. A humanized antibody of the isolated monoclonal antibody produced by the hybridoma deposited with the ATCC under Accession Number PTA-4621, or an antigen binding fragment produced of said humanized antibody.

10. The isolated monoclonal antibody or antigen binding fragments of claim 8 conjugated with a member selected from the group consisting of cytotoxic moieties, enzymes, radioactive compounds, and hematogenous cells.

11. A chimeric antibody of the isolated monoclonal antibody or produced by the hybridoma deposited with the ATCC under Accession Number PTA-4621, or is an antigen binding fragment produced of said humanized antibody.

12. The isolated hybridoma deposited with the ATCC under Accession Number PTA-4621.

13. A binding assay to determine the presence of cancerous cells in a human tissue sample selected from the group consisting of human colon, ovarian, lung, and breast tissue samples comprising:

providing said human tissue sample;

providing the isolated monoclonal antibody produced by the hybridoma deposited with the ATCC under Accession Number PTA-4621, or an antigen binding fragment produced from said isolated monoclonal antibody;

contacting said isolated monoclonal antibody or said antigen binding fragment with said human tissue sample; and determining binding of said isolated monoclonal antibody or said antigen binding fragment with said human tissue sample; whereby the presence of said cancerous cells in said human tissue sample is indicated.

* * * * *